United States Patent
Boaz et al.

(10) Patent No.: US 6,337,418 B1
(45) Date of Patent: Jan. 8, 2002

(54) PREPARATION OF $C_1$-$C_5$ ALKYL ESTERS OF NITRO OR THIOETHER SUBSTITUTED AROMATIC CARBOXYLIC ACIDS

(75) Inventors: Neil W. Boaz, Kingsport, TN (US); M. Todd Coleman; Timothy R. Hightower, both of Batesville, AR (US)

(73) Assignee: Eastman Chemical Co., Kingsport, TN (US)

( * ) Notice: Subject to any disclaimer, the term of this patent is extended or adjusted under 35 U.S.C. 154(b) by 0 days.

(21) Appl. No.: 09/288,642

(22) Filed: Apr. 9, 1999

(51) Int. Cl.$^7$ ............................................. C07C 205/06
(52) U.S. Cl. .............................. 560/20; 560/11; 560/12; 560/18
(58) Field of Search .............................. 560/11, 12, 18, 560/20

(56) References Cited

U.S. PATENT DOCUMENTS

| | | | |
|---|---|---|---|
| 4,102,920 A | 7/1978 | Bartish | 260/532 |
| 4,374,262 A | 2/1983 | McGinnis et al. | 560/56 |
| 4,506,092 A | 3/1985 | Lentz et al. | 560/103 |
| 4,507,493 A | 3/1985 | Lentz et al. | 560/103 |
| 4,704,467 A | 11/1987 | Wehrenberg | 560/11 |
| 5,344,992 A | 9/1994 | Drewes et al. | 568/314 |

FOREIGN PATENT DOCUMENTS

| | | |
|---|---|---|
| EP | 0 454 624 A1 | 10/1991 |
| EP | 0 470 856 A1 | 2/1992 |
| EP | 0 697 390 A1 | 2/1996 |
| JP | 2-45448 | 2/1990 |
| JP | 4-193847 | 7/1992 |
| JP | 4-193848 | 7/1992 |
| JP | 4-193849 | 7/1992 |
| WO | WO 95/00476 | 1/1995 |
| WO | WO 95/24372 | 9/1995 |
| WO | WO 97/28122 | 8/1997 |
| WO | WO 98/55438 | 12/1998 |
| WO | WO 99/02489 | 1/1999 |
| WO | WO 99/32463 | 7/1999 |

OTHER PUBLICATIONS

Sunderman, R., et al., "Reductive Carbonylation of Nitro Compounds", *Applied Homogeneous Catalysis with Organometallic Compounds*, vol. 2, pp. 1072–1080 (1996).

Schoenberg et al., "Palladium–Catalyzed Carboalkoxylation of Aryl, Benzyl, and Vinylic Halides", *J. Org. Chem.,* vol. 39, pp. 3318–3326 (1974).

Takeuchi et al., "Platinum Complex–catalysed Carbonylations of Organic Iodides having β–Hydrogens attached to sp$^3$–Carbons", *J. Chem. Soc., Chem. Commun.,* pp. 351–352 (1986).

*Primary Examiner*—Paul J. Killos
*Assistant Examiner*—Robert W. Deemie
(74) *Attorney, Agent, or Firm*—Michael J. Blake Esq.; Bernard J. Graves

(57) ABSTRACT

Methods for preparing substituted aromatic carboxylic acid esters are described. In particular, the invention relates a method for preparing a nitro-substituted aromatic carboxylic acid ester:

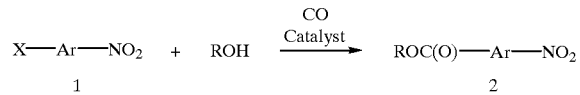

Additionally the invention relates to a method for preparing a thioether-substituted aromatic carboxylic acid ester:

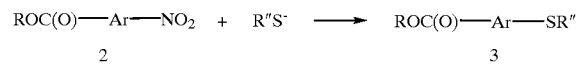

Such aryl esters are useful in the preparation of various agrochemicals and agrochemical intermediates.

16 Claims, No Drawings

PREPARATION OF $C_1$-$C_5$ ALKYL ESTERS OF NITRO OR THIOETHER SUBSTITUTED AROMATIC CARBOXYLIC ACIDS

BACKGROUND OF THE INVENTION

1. Field of the Invention

The invention relates a process for the preparation of substituted aromatic carboxylic acid esters. In particular the invention relates a process for the preparation of nitro-substituted aromatic carboxylic acid esters and thioether-substituted aromatic carboxylic acid esters. Such aryl esters are useful intermediates in the preparation of agrochemicals and agrochemical intermediates.

2. Description of the Related Art

Aryl 1,3-diketones are important synthetic intermediates for a variety of industrially-produced chemicals, such as herbicidal isoxazol derivatives. For example, EP 470856 describes various herbicidal isoxazole derivatives and a process for their preparation from aryl 1,3-diketones. WO 97/28122 describes the preparation of 1-aryl-3-cyclopropyl-1,3-diketones as intermediates used to prepare agrochemicals (e.g. herbicides, pesticides). These 1,3-diketones can be prepared by reacting a substituted acetophenone with a cyclopropanecarboxylic acid ester. However, in addition to the difficulty of preparing the starting substituted acetophenone, the reaction only affords a moderate yield of the desired 1,3-diketone. Aryl 1,3-diketones can also be prepared, as described in WO 95/00476, by hydrolysis of β-aminovinyl ketones resulting from the reaction between a ketone and a substituted benzonitrile. WO 95/00476 also discloses that reacting a ketone with a substituted benzoic acid ester (prepared from the hydrolysis and subsequent esterification of an aromatic nitrile) also leads to the formation of aryl 1,3-diketones.

Preparation of benzoate esters by the metal-catalyzed carbonylation of an unsubstituted aryl halide substrate, especially an aryl iodide substrate, in alcohol is a well-known process. See, e.g Schoenberg et al, *J. Org. Chem.*, 39, 3318 (1974); Stille and Wong, *J. Org. Chem.*, 40, 532 (1975); Takeuchi et al, *J. Chem. Soc., Chem. Commun.*, 351 (1986); Hicai et al, *Bull. Chem. Soc. Jpn*, 48, 2075 (1975); Ito et al, *Bull. Chem. Soc. Jpn.*, 48, 2091 (1975); Takahashi et al, *Chem. Lett.*, 369 (1980). While aryl bromide substrates are moderately active in such reactions, aryl chlorides are generally inert, although limited success has been achieved with aryl chloride substrates using customized catalysts.

Metal-catalyzed reductive carbonylation of nitroaromatic compounds in alcohol is also a well-known process. Sundermann, R., et al., *Appl. Homogeneous Catal. Organomet. Compd.*, 2, 1072–1080 (1996). Under such reaction conditions reduction of the nitro group results affording aniline derivatives or related compounds. For example, the reaction of nitroarenes with carbon monoxide in alcohols with catalytic rhodium complexes results in the formation of urethanes. Id. Accordingly, since the nitro group is prone to reduction, the metal-catalyzed carbonylation of aromatic substrates substituted with both a halo and a nitro group in alcohols is generally avoided.

Thus there still exists a need in the art for a method of preparing nitro-substituted aromatic carboxylic acid esters from nitro-substituted aryl halide substrates under metal-catalyzed carbonylation reaction conditions without reduction of the nitro group. Such compounds are useful precursors for the preparation of 1,3-diketone agrochemical intermediates.

SUMMARY OF THE INVENTION

The invention answers the need in the art by providing a simple and efficient process to prepare nitro-substituted aromatic carboxylic acid esters from nitro-substituted aryl halides. More particularly, the invention provides a process for the preparation of a nitro-substituted aromatic carboxylic acid ester by reacting a nitro-substituted aryl halide, in the absence of water and oxygen, with carbon monoxide and an alcohol in the presence of a metal catalyst and a proton acceptor.

The invention also provides a simple and efficient process for the preparation of a thioether-substituted aromatic carboxylic acid ester from a nitro-substituted aromatic carboxylic acid ester. Specifically, the process of the invention involves reacting a nitro-substituted aromatic carboxylic acid ester with a thiolate anion.

The invention further provides a one-pot synthesis of a thioether-substituted aromatic carboxylic acid ester from a nitro-substituted aryl halide. According to the invention, a one-pot synthesis reacts a nitro-substituted aryl halide is reacted, in the absence of water and oxygen, with carbon monoxide and an alcohol in the presence of a metal catalyst and a proton acceptor to form the corresponding nitro-substituted aromatic carboxylic acid ester. Without being isolated, the nitro-substituted aromatic carboxylic acid ester is then reacted with a thiolate anion to form the corresponding thioether-substituted aromatic carboxylic acid ester.

DETAILED DESCRIPTION OF THE INVENTION

The invention relates to a process for the preparation of a nitro-substituted aromatic carboxylic acid ester under metal-catalyzed carbonylation reaction conditions. In particular, the invention relates to a process for the preparation of a nitro-substituted aromatic carboxylic acid ester in which a nitro-substituted aryl halide is reacted, in the absence of water and oxygen, with carbon monoxide and an alcohol in the presence of a metal catalyst and a proton acceptor to form the corresponding nitro-substituted aromatic carboxylic acid ester. According to a process of the invention, the halide of the nitro-substituted aryl halide is replaced with or converted to an ester group with little to no, i.e. minimal, reduction of the nitro group. The process is outlined in Scheme A below:

Scheme A

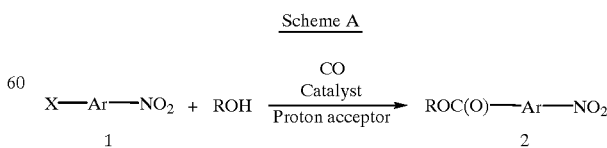

The nitro-substituted aryl halide 1 may be any aryl halide substituted with at least one nitro group known in the art. The halide (X) of the nitro-substituted aryl halide 1 may be a halo group such as, for example, chloro, bromo, or iodo. The aryl group (Ar) may be a monocyclic or polycyclic aryl group or a monocyclic or polycyclic heteroaryl group containing at least one heteroatom of N, O, or S. Examples of suitable aryl groups include, for example, phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indazolyl, purinyl, isoquinolyl, quinolyl, isothiazolyl, isoxazolyl, phthalazinyl, quinoxalinyl, quinazolinyl, benzothienyl, isoindolyl, anthryl, phenanthryl, and the like. The aryl group (Ar) of the nitro-substituted aryl halide 1 may also be further substituted with, for example, substituents R'. As discussed here, R' may be linear or branched, substituted or unsubstituted. Possible R' substituents include, but are not limited to, $C_1$–$C_{10}$alkyl, $C_2$–$C_{10}$ alkenyl, $C_2$–$C_{10}$ alkynyl, $C_4$–$C_{10}$ aryl or heteroaryl, ether, thioether, nitro, trifluoromethyl, fluoro, cyano, and acyl group.

According to the invention, the nitro-substituted aryl halide 1 contains at least one nitro group. Any one nitro group may be adjacent to or at any other position relative to the halo group on the aryl group. For example, if the aryl group is a phenyl group, a nitro group may be substituted at the ortho-, meta-, or para- position. In a preferred embodiment of the invention, the nitro-substituted aryl halide 1 is an ortho-substituted aryl halide, ie. at least one nitro group is ortho to the halo group.

In a preferred embodiment of the invention, the nitro-substituted aryl halide 1 is a nitro-substituted aryl halide of formula (I):

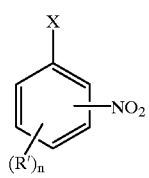

(I)

In formula (I), X is a halo group as described above, n is an integer from 1–4, and R' is, independently, as described above or may together with the phenyl group form a substituted or unsubstituted fused polycyclic ring system. In a more preferred embodiment of the invention, in formula (I), n is 1 and R' is a trifluoromethyl group. In another more preferred embodiment of the invention, in formula (I), n is 1, R' is a trifluoromethyl group and is para to halide X, and the nitro group is ortho to halide X.

A process of the invention should be carried out under sufficient carbon monoxide (CO) pressure to permit facile conversion of the nitro-substituted aryl halide 1. The conversion should take place in the substantial absence of water and oxygen. Preferably, the CO pressure may range from about 14.7–1100 psi (about 1–75 atm), and more preferably from about 14.7–514 psi (about 1–35 atm). In addition to carbon monoxide, inert gases that do not interfere with the conversion of the nitro-substituted aryl halide 1 to the corresponding nitro-substituted aromatic carboxylic acid ester 2 such as, for example, helium, argon, and nitrogen, may also be present.

The alcohol employed is selected depending upon the desired nitro-substituted aromatic carboxylic acid ester 2. The alcohol is of the general formula ROH where R is a $C_1$–$C_5$ alkyl group, i.e. the alcohol is a $C_1$–$C_5$ alcohol. As discussed here, R may be linear or branched, substituted or unsubstituted. Examples of suitable alcohols include, but are not limited to, methanol, n-butanol, and isopropanol. Preferably, the alcohol is methanol or n-butanol. The amount of alcohol used may vary ranging from about 1.0 equivalent to an excess of alcohol, preferably about 1–100 equivalents, based on the nitro-substituted aryl halide 1.

The metal catalyst may be any metal catalyst which allows carbonylation of a nitro-substituted aryl halide without reduction of the nitro group. In a preferred embodiment, the metal catalyst is a transition metal catalyst. Examples of suitable transition metals include, but are not limited to, palladium, platinum, cobalt, nickel, iron, rhodium, ruthenium and the like. Preferably, the catalyst is a palladium metal catalyst.

The catalyst may be either homogeneous or heterogeneous in nature. If homogeneous, the catalyst is preferably complexed by donor ligands such as phosphines. For example, useful homogeneous catalysts include dihalobis (triphenylphosphine)palladium species such as dichlorobis (triphenylphosphine)palladium and dibromobis (triphenylphosphine)palladium. The amount of homogeneous catalyst used may generally vary from between about 0.0005 and about 0.5 equivalents based on the nitro-substituted aryl halide 1 substrate, with more catalyst leading to a faster reaction. If the catalyst is heterogeneous, the metal can be used alone or supported on an inert matrix such as activated carbon (e.g. palladium metal deposited on activated carbon (Pd/C)). The loading of the support can vary between about 1 and about 30 percent (e.g., 1% palladium on carbon to 30% palladium on carbon). The amount of heterogeneous catalyst used may generally vary from between about 1 and about 500 weight percent based on the amount of nitro-substituted aryl halide 1 substrate. More preferably, between about 1–100 weight percent and most preferably, between about 5–50 weight percent, based on the amount of nitro-substituted aryl halide 1 substrate.

The catalyst may be preformed or may be formed in situ from appropriate precursors. For example, phosphine and palladium metal catalysts may be prepared in situ from a suitable palladium source and one or more phosphines, preferably using between about 1 and about 6 atom equivalents of phosphorus per atom equivalent of palladium. Examples of suitable palladium sources include, but are not limited to, palladium(II) acetate, palladium(II) chloride, dichlorobis(acetonitrile)palladium(II), dichlorobis (benzonitrile)palladium(II), bis(dibenzylidineacetone) palladium(0), tris(dibenzylidineacetone)dipalladium(0), tris (dibenzylidineacetone)dipalladium(0) chloroform adduct and the like. Examples of suitable phosphines include, but are not limited to, monophosphines such as, for example, trimethylphosphine, triethylphosphine, tri-n-propylphosphine, tri-i-propylphosphine, tri-n-butylphosphine, tri-t-butylphosphine, tricyclohexylphosphine, triphenylphosphine, tri-o-tolylphosphine, methyldiphenylphosphine and the like and diphosphines such as, for example, 1,2-bis (diphenylphosphinoethane), 1,3-bis(diphenylphosphino) propane and the like.

The proton acceptor may be any suitable proton acceptor known in the art such as, for example, sodium acetate, sodium bicarbonate, and disodium phosphate. The proton acceptor may also be a tertiary amine base such as a trialkylamine base. Examples of suitable tertiary amine bases include, for example, triethylamine and tri-n-butylamine. The amount of proton acceptor used may vary and range from between about 1–5 equivalents, preferably between about 1.2–2.0 equivalents.

According to the invention, conversion of a nitro-substituted aryl halide 1 to the corresponding nitro-substituted aromatic carboxylic acid ester 2 is generally conducted in the presence of a solvent. The solvent may be an excess of the alcohol used as a reactant as described above. Likewise the solvent may also be an excess amount of the proton acceptor, as described above. The solvents may be other than the alcohol or the proton acceptor as well. For example, the solvent may be an aliphatic hydrocarbon, aromatic hydrocarbon, cyclic or acyclic ether, polar aprotic solvent or a mixture thereof. Examples of suitable aliphatic hydrocarbons include, but are not limited to, hexane, heptane, octane and mixtures thereof. Examples of suitable aromatic hydrocarbons include, but are not limited to, toluene, xylenes, chlorobenzene and mixtures thereof. Examples of suitable cyclic or acyclic ethers include, but are not limited to, tert-butyl methyl ether, diisopropyl ether, tetrahydrofuran and mixtures thereof. Suitable polar aprotic solvents include, but are not limited to, dimethylformamide, dimethyl sulfoxide, N-methylpyrrolidone and mixtures thereof.

The reaction can be run at atmospheric pressure or at elevated pressure. Preferably, the reaction is run at a total pressure of between about 1–200 atmospheres. More preferably, the reaction is run at a total pressure of between about 1–75 atmospheres, and most preferably, between about 1–35 atmospheres.

The reaction should be run at a temperature sufficient to effect facile conversion of 1 to 2. In general, the temperature may be varied generally between about ambient temperature and the boiling point (or apparent boiling point at elevated pressure) of the lowest boiling component (e.g. solvent) of the reaction mixture. Preferably, the conversion of 1 to 2 may be performed at temperatures ranging from between about room temperature to about 200° C. Likewise the reaction may be run for a length of time sufficient to affect conversion of 1 to 2 and may vary based on the temperature and pressure, each as described above.

Reacting a preferred nitro-substituted aryl halide of formula I, in the absence of water and oxygen, with carbon monoxide and an alcohol in the presence of a catalyst and a proton acceptor according to the invention results in a nitro-substituted aromatic carboxylic acid ester of formula (II):

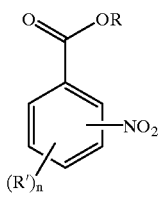

In formula (II), R and R' are each as described above. In a more preferred embodiment of the invention, in formula (II), R is a methyl or n-butyl group, n is 1, and R' is a trifluoromethyl group. In another more preferred embodiment of the invention, in formula (II), R is a methyl or n-butyl group, n is 1, R' is a trifluoromethyl group and is para to the ester group, and the nitro group is ortho to the ester group.

In another embodiment of the invention, a nitro-substituted aromatic carboxylic acid ester 2, as described above, may be reacted with a thiolate anion (R"S$^-$) to form a thioether-substituted aromatic carboxylic acid ester 3. Such a process is outlined in Scheme B as follows:

Scheme B

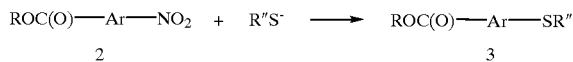

The thiolate anion may be preformed or prepared in situ from a thiol and a base. The thiol may be neutral thiol, as described below. The base may be any suitable base capable of generating the anion of the thiol such as, for example, tertiary amines, and alkali or alkaline earth metal hydroxides or carbonates.

According to the invention, the thiolate anion R"S$^-$ replaces or displaces the nitro group of the nitro-substituted aromatic carboxylic acid ester 2 to give the corresponding thioether-substituted aromatic carboxylic acid ester 3. The thiolate anion can be introduced into the reaction as either a neutral thiol, R"SH, and an appropriate base or, more preferably, as a salt of a thiolate anion, R"S$^-$, with a corresponding counterion, M$^+$, of sodium, potassium, ammonium and the like. R" may be a $C_1$–$C_{10}$ alkyl group or a $C_4$–$C_{10}$ aryl or heteroaryl group containing at least one heteroatom of N, O or S. As discussed here, R" may be linear or branched, substituted or unsubstituted. Possible substituents include, but are not limited to, alkyl, alkenyl, alkynyl, hydroxy, cyano, ether, and thioether groups. Examples of suitable R" groups include, but are not limited to, methyl, ethyl, n-propyl, i-propyl, phenyl, and naphthyl groups. Preferably, the thiolate anion is sodium thiomethoxide.

Conversion of the nitro-substituted aromatic carboxylic acid ester 2 to the thioether-substituted aromatic carboxylic acid ester 3 may be performed by any means that promotes displacement of the nitro group with a thioether group. Preferably, such conversion is conducted in a homogeneous solvent system or a phase-transfer solvent system. More preferably, such conversion is conducted in a phase-transfer solvent system. A homogeneous solvent system is based on a mixture of water and a water-soluble solvent. Suitable water-soluble solvents include, but are not limited to, ketones (e.g. acetone or other dialkyl ketones), lower alcohols (e.g. $C_1$–$C_4$ alcohols), formamide, dimethyl formamide, dimethyl sulfoxide, N-methylpyrrolidone and the like and mixtures thereof. A phase-transfer solvent system is based on a phase transfer catalyst in a water-immiscible solvent and, optionally, water. Water-immiscible solvents include aliphatic hydrocarbons (e.g. hexane, heptane, octane), aromatic hydrocarbons (e.g. toluene, xylenes, chlorobenzene), cyclic or acyclic ethers (e.g. tert-butyl methyl ether, diisopropyl ether, diethoxymethane) and mixtures thereof. The phase-transfer catalyst is chosen from readily available ammonium or phosphonium salts such as tetrabutylammonium bromide, tetrabutylammonium chloride, methyltributylammonium chloride, methyl trioctylammonium chloride, tetrabutylphosphonium bromide and the like. Preferably, the phase transfer catalyst is tetrabutylammonium bromide.

The temperature of and the length of time for the reaction of a nitro-substituted aromatic carboxylic acid ester 2 with a thiolate anion, as described above, to form a thioether-substituted aromatic carboxylic acid ester 3 may be varied depending upon the nature of the reactants. Generally, the reaction temperature is ambient temperature and the reaction time ranges between about 1–24 hours, preferably between about 1–12 hours, more preferably between about 1–3 hours.

In a preferred embodiment of the invention, reacting a preferred nitro-substituted aromatic carboxylic acid ester of formula II with a thiolate anion (R"S$^-$) results in a thioether-substituted aromatic carboxylic acid ester 3 of formula (III):

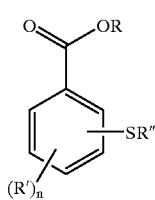

(III)

In formula (III), R, R', and n are each as described above and R" is a branched or linear, substituted or unsubstituted $C_1$–$C_{10}$ alkyl group or a substituted or unsubstituted $C_4$–$C_{10}$ aryl or heteroaryl group, each as described above. In a more preferred embodiment of the invention, in formula (III), R is a methyl or n-butyl group, n is 1, R' is a trifluoromethyl group, and R" is a methyl group. In another more preferred embodiment of the invention, in formula (III), R is a methyl or n-butyl group, n is 1, R' is a trifluoromethyl group and is para to the ester group, and R" is a methyl group such that the SR" group is ortho to the ester group.

The invention further relates an efficient one-pot, two-step synthesis of a thioether-substituted aromatic carboxylic acid ester 3 from a nitro-substituted aryl halide 1, each as described above, and is illustrated in Scheme C below. According to the invention, a nitro-substituted aryl halide 1 is reacted, in the absence of water and oxygen, with carbon monoxide and an alcohol in the presence of a metal catalyst and a proton acceptor to form a reaction mixture containing the corresponding nitro-substituted aromatic carboxylic acid ester 2, all as described above. Without isolating the nitro-substituted aromatic carboxylic acid ester 2, it is then reacted with a thiolate anion to form the corresponding thioether-substituted aromatic carboxylic acid ester 3, also all as described above. In a preferred embodiment of a one-pot synthesis of the invention, the reaction between the nitro-substituted aromatic carboxylic acid ester 2 and thiolate anion to form the corresponding thioether-substituted aromatic carboxylic acid ester 3 is conducted in phase transfer solvent system as described above.

Scheme C

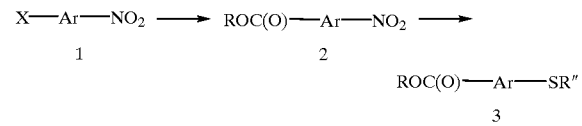

In a preferred embodiment of a one-pot synthesis of the invention, a nitro-substituted aryl halide of formula (I) is reacted, in the absence of water and oxygen, with carbon monoxide and an alcohol in the presence of a catalyst and a proton acceptor to form the corresponding nitro-substituted aromatic carboxylic acid ester of formula (II). The nitro-substituted aromatic carboxylic acid ester of formula (II), without being isolated, is then reacted with a thiolate anion to form a thioether substituted aromatic carboxylic acid ester of formula (III). Such a process is outlined in Scheme D:

Scheme D

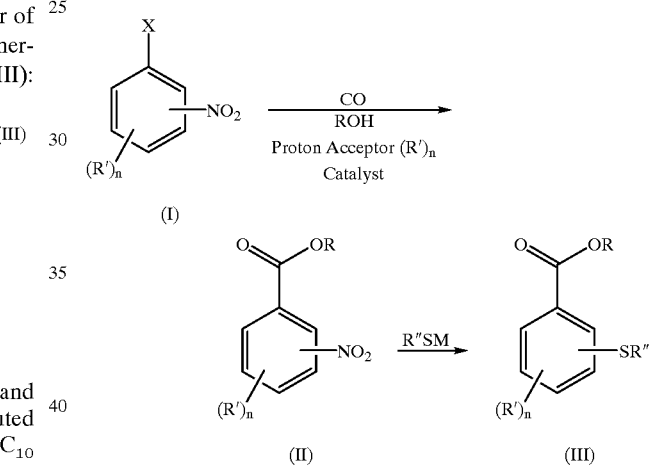

In Scheme D, X, R, R', R", M$^+$, n, proton acceptor, and catalyst are each as described above.

In another preferred embodiment of the one-pot synthesis of the invention, a nitro-substituted aryl halide of formula (I) is reacted, in the absence of water and oxygen, with carbon monoxide and an alcohol in the presence of a catalyst and a proton acceptor to form the corresponding nitro-substituted aromatic carboxylic acid ester of formula (II). Without isolation, the corresponding nitro-substituted aromatic carboxylic acid ester of formula (II) may then be reacted with a thiolate anion in a phase transfer solvent system, as described above, to form the corresponding thioether substituted aromatic carboxylic acid ester of formula (III).

To prepare useful aryl 1,3-diketone compounds, such as those discussed above, the thioether-substituted aromatic carboxylic acid ester 3 may be readily converted to a 1,3-diketone by Claisen condensation with a ketone such as, for example, cyclopropyl methyl ketone. The Claisen condensation is a well-known reaction, and there are many methods to affect this condensation reaction. Hauser et al., *Organic Reactions* 8:59 (1954); Reuther et al., EP 697 390; Krbechek et al., WO 95/24372; Drewes et al., EP 454 624;

Bloomfield, J. J., J. Org. Chem. 27:2742 (1962); Anselme, J. P., *J. Org. Chem.* 32:3716 (1967); Drewes et al., U.S. Pat. No. 5,344,992; Boaz: et al., WO 98155438.

All references including patents cited herein are each incorporated in their entirety by reference. A further understanding can be obtained by reference to certain specific examples which are provided herein for purpose of illustration only and are not intended to be limiting unless otherwise specified.

EXAMPLES

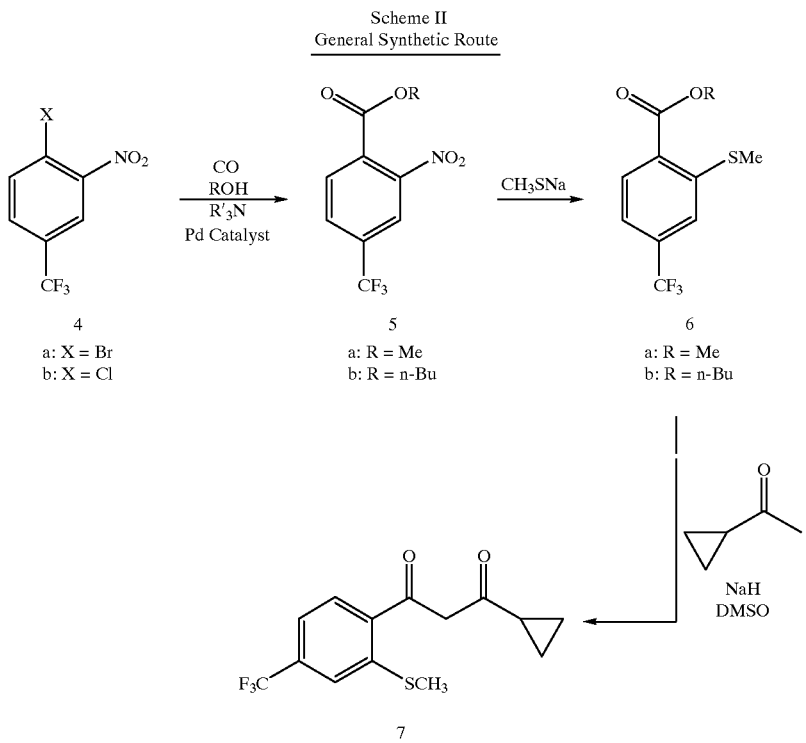

Example 1

Preparation of Methyl 2-Nitro-4 trifluoromethylbenzoate (5a)

Dichlorobis(triphenylphosphine)palladium (210 mg; 0.30 mmol; 0.015 equiv) was added to a 100-mL flask equipped with magnetic stirrer. The flask was evacuated and filled with carbon monoxide (14.7 psi; 1 atm). A mixture of 4-bromo-3-nitrobenzotrifluoride (4a; 3.06 mL; 20 mmol), triethylamine (3.5 mL; 25 mmol; 1.25 equiv) and methanol (2.4 mL; 60 mmol; 3 equiv) was added and the mixture was evacuated and filled with carbon monoxide four times.

The reaction mixture was heated to 60° C. under a carbon monoxide atmosphere (14.7 psi; 1 atm) for 15 h. The mixture was diluted with ethyl acetate and washed twice with 3 N HCl and once with saturated aqueous sodium bicarbonate. The organic solution was dried over $MgSO_4$ and concentrated to afford 5.04 g of crude product which showed a ratio of 4a:5a of 82:18 by $^1H$ NMR analysis. The crude product was flash-chromatographed using 1:9 ethyl acetate:heptane for elution. This afforded 0.88 g (17.7%; 98% based on conversion) of 5a.

$^1H$ NMR (CDCl$_3$) δ 8.212 (s, 1H); 7.954 (dd, 1H; J=0.84,7.97 Hz); 7.876 (d, 1H, J=7.97 Hz); 3.962 (s, 3H). IR (neat film) 1750 cm$^{-1}$. FDMS: m/e 249 (M$^+$).

Example 2

Preparation of Methyl 2-Nitro 4-trifluoromethylbenzoate (5a) at Elevated Pressure Dichlorobis(triphenylphosphine)palladium (70 mg; 0.10 mmol; 0.005 equiv) was added to a 100-mL autoclave. A mixture of 4-bromo-3-nitrobenzotrifluoride (4a; 3.06 mL; 20 mmol), triethylamine (3.5 mL; 25 mmol; 1.25 equiv), and methanol (60 mL; ~75 equiv.) was added and the mixture was pressurized and purged with helium three times and carbon monoxide four times. The reaction mixture was placed under 60 psi CO and heated to 100° C. for 8.5 h, during which time the pressure was maintained between 50 and 75 psi by the addition of carbon monoxide as necessary. The mixture was cooled and vented and the solvent was stripped. The residue was diluted with toluene and washed with 3 N HCl (10 mL) and saturated aqueous sodium bicarbonate. The organic solution was dried with sodium sulfate and concentrated to afford 4.13 g of crude product which showed complete conversion of 4a to 5a by $^1H$ NMR analysis.

$^1H$ NMR (CDCl$_3$) δ 8.212 (s, 1H); 7.954 (dd, 1H; J=0.84, 7.97 Hz); 7.876 (d, 1H, J=7.97 Hz); 3.962 (s, 3H).

Example 3

Preparation of Methyl 2-Nitro-4-trifluoromethylbenzoate (5a) using a Heterogeneous Catalyst 5% Palladium on carbon (270 mg; 10 wt % based on 4a) was added to a 100-mL autoclave. A mixture of 4-bromo- 3-nitrobenzotrifluoride (4a; 1.53 mL; 10 mmol), triethylamine (1.75 mL; 12.5 mmol; 1.25 equiv), and methanol (60 mL; ~75 equiv.) was added and the mixture was pressurized and purged with helium three times and carbon monoxide four times. The reaction mixture was placed under 60 psi CO and heated to 100° C. for 13 h, during which time the pressure was maintained between 50 and 75 psi by the addition of carbon monoxide as necessary. The mixture was cooled, vented, and filtered through celite and eluted with methanol to remove the catalyst. The volatiles were stripped and the residue was diluted with toluene and washed with 3 N HCl (10 mL) and water. The organic solution was dried with sodium sulfate and concentrated to afford 2.12 g of crude product which showed 23% conversion of 4a to 5a by $^1$H NMR analysis.

$^1$H NMR (CDCl$_3$) δ 8.212 (s, 1H); 7.954 (dd, 1H; J=0.84, 7.97 Hz); 7.876 (d, 1H, J=7.97 Hz); 3.962 (s, 3H).

Example 4

Preparation of Butyl 2-Nitro-4-trifluoromethylbenzoate (5b) at Elevated Pressure Dichlorobis(triphenylphosphine)palladium (70 mg; 0.10 mmol; 0.005 equiv) was added to a 100-mL autoclave. A mixture of 4-bromo-3-nitrobenzotrifluoride (4a; 3.06 mL; 20 mmol), triethylamine (3.5 mL; 25 mmol; 1.25 equiv), and n-butanol (60 mL; ~33 equiv.) was added and the mixture was pressurized and purged with helium three times and carbon monoxide four times. The reaction mixture was placed under 60 psi CO and heated to 100° C. for 10 h, during which time the pressure was maintained between 50 and 75 psi by the addition of carbon monoxide as necessary. The mixture was cooled and vented and the solvent was stripped. The residue was diluted with toluene and washed with 3 N HCl (10 mL) and saturated aqueous sodium bicarbonate. The organic solution was dried with sodium sulfate and concentrated to afford 5.46 g (93%) of 5b (no residual 4a by GC and $^1$H NMR analysis).

$^1$H NMR (CDCl$_3$) δ 8.193 (s, 1H); 7.943 (dd, 1H; J=1.10, 7.97 Hz); 7.877 (d, 1H, J=7.97 Hz); 4.365 (t, 2H, J=6.52 Hz); 1.715 (m, 2H); 1.400 (m, 2 H); 0.955 (t, 3H, J=7.14 Hz). IR (neat film): 1740 cm$^{-1}$(s); 1550 cm$^{-1}$ (s). FDMS: m/e 292 (M$^+$1).

Example 5

Preparation of Methyl 2-Nitro-4-trifluoromethylbenzoate (5a) from 4-Chloro-3-Nitrobenzotrifluoride (4b)

Dichlorobis(triphenylphosphine)palladium (105 mg; 0.30 mmol; 0.015 equiv) was added to a 100-mL flask equipped with magnetic stirrer. The flask was evacuated and filled with carbon monoxide (14.7 psi; 1 atm). A mixture of 4-chloro-3-nitrobenzotrifluoride (4b; 1.50 mL; 10 mmol), triethylamine (1.75 mL; 12.5 mmol; 1.25 equiv) and methanol (10 mL; ~25 equiv.) was added and the mixture was evacuated and filled with carbon monoxide four times. The reaction mixture was heated to 60° C. under carbon monoxide (14.7 psi; 1 atm) for 24 h. The mixture was diluted with ethyl acetate and toluene and washed with 3 N HCl (10 mL) and water (10 mL). The organic solution was dried with sodium sulfate and concentrated to afford 2.31 g of crude product that showed 5% conversion of 4b to 5a according to $^1$H NMR analysis.

$^1$H NMR (CDCl$_3$) δ 8.212 (s, 1H); 7.954 (dd, 1H; J=0.84, 7.97 Hz); 7.876 (d, 1H, J=7.97 Hz); 3.962 (s, 3H).

Example 6

Phase-Transfer Preparation of Methyl 2-Methylthio-4-trifluoromethylbenzoate (6a)

Sodium thiomethoxide (91 mg; 1.3 mmol; 1.3 equiv) was dissolved in water (0.34 mL). Tetrabutylammonium bromide (48 mg; 0.15 mmol; 0.15 equiv) was added. Methyl 2-nitro-4-trifluoromethylbenzoate (5a; 249 mg; 1.0 mmol) was dissolved in toluene and added to the mixture. The reaction mixture was stirred at ambient temperature for 1 h to completely consume 5a according to gas chromatography (GC) analysis. The reaction mixture was diluted with ethyl acetate and water and the layers were thoroughly mixed and then separated. The organic layer was dried over Na$_2$SO$_4$ and concentrated to afford 0.26 g of 6a which contained a small amount of tetrabutylammonium bromide. The crude product was filtered through a pad of flash silica gel to afford 226 mg (90%) of 6a.

$^1$H NMR (CDCl$_3$) δ 8.089 (d, 1H, J=8.24 Hz); 7.400 (d, 1H; J=1.10); 7.377 (dd, 1H, J=1.10, 8.24); 3.939 (s, 3H); 2.492 (s, 3H). IR (neat film): 1730 cm$_1$(s). FDMS: 250 (M$^+$).

Example 7

Single Phase Preparation of Methyl 2-Methylthio-4-trifluorometh lbenzoate (6a)

Sodium thiomethoxide (91 mg; 1.3 mmol; 1.3 equiv) was dissolved in water (0.34 mL) and the solution was cooled in ice-water. Methyl 2-nitro4-trifluoromethylbenzoate (5a; 249 mg; 1.0 mmol) was dissolved in acetone and added to the mixture. The reaction mixture was stirred at ambient temperature for 1 h to completely consume 5a according to gas chromatography (GC) analysis. The reaction mixture was diluted with ethyl acetate and brine and the layers were thoroughly mixed and then separated. The aqueous layer was extracted with a further portion of ethyl acetate. The combined organic solution was dried with magnesium sulfate and concentrated to afford 0.11 g of crude product that was largely 6a according to $^1$H NMR analysis.

$^1$H NMR (CDCl$_3$) δ 8.089 (d, 1H, J=8.24 Hz); 7.400 (d, 1H; J=1.10); 7.377 (dd, 1H, J=1.10, 8.24); 3.939 (s, 3H); 2.492 (s, 3H).

Example 8

Phase-Transfer Preparation of Butyl 2-Methylthio-4-trifluoromethylbenzoate (6b)

Sodium thiomethoxide (0.91 g; 13.0 mmol; 1.3 equiv) was dissolved in water (3.4 mL). Tetrabutylammonium bromide (0.48 g; 1.50 mmol; 0.15 equiv) was added. Butyl 2-nitro-4-trifluoromethylbenzoate (5b; 2.91 g; 10.0 mmol) was dissolved in toluene (5 mL) and added to the mixture. The reaction mixture was stirred at ambient temperature for 2.5 h to completely consume 5b according to thin layer chromatography (tlc) analysis. The reaction mixture was diluted with toluene and water and the layers were thoroughly mixed and then separated. The organic layer was dried over $Na_2SO_4$ and concentrated to afford 2.85 g (98%) of 6b which contained a small amount of tetrabutylammonium bromide. The crude product was flash chromatographed and eluted with 5% ethyl acetate in heptane to afford 2.32 g (79%) of pure 6b.

$^1$H NMR (CDCl$_3$) δ 8.086 (d, 1H, J=7.69 Hz); 7.463 (s, 1H); 7.382 (dm, 1H, J=8.24 Hz); 4.354 (t, 2H, J=6.59 Hz); 2.495 (s, 3H); 1.77 (m, 2H); 1.49 (m, 2H); 0.975 (t, 3H, J=7.42 Hz). IR (neat film): 1720 cm$^{-1}$(s). FDMS: m/e 292 (M$^+$)

Example 9

Preparation of Methyl 2-Methylthio-4-trifluoromethylbenzoate (6a) without Isolation of Methyl 2-Nitro-4-trifluoromethylbenzoate (5a)

Dichlorobis(triphenylphosphine)palladium (140 mg; 0.20 mmol; 0.01 equiv) was added to a 100-mL autoclave. A mixture of 4-bromo-3-nitrobenzotrifluoride (4a; 3.06 mL; 20 mmol), triethylamine (3.5 mL; 25 mmol; 1.25 equiv), and methanol (60 mL; 75 equiv) was added and the mixture was pressurized and purged with helium three times and carbon monoxide (CO) four times. The reaction mixture was placed under 60 psi carbon monoxide and heated to 100° C. for 6 h, during which time the pressure was maintained between 50 and 75 psi by the addition of carbon monoxide as necessary. The mixture was cooled and vented and the bulk of the solvent was distilled at reduced pressure. Water (10 mL), toluene (15 mL) and 3 N HCl (10 mL) were added and the mixture was filtered to remove fine particulates. The layers were separated and the organic layer was washed with aqueous sodium bicarbonate (10 mL). The organic solution was then added to a mixture of sodium thiomethoxide (1.82 g; 26 mmol; 1.3 equiv) and tetrabutylammonium bromide (0.64 g; 2.0 mmol; 0.10 equiv) dissolved in water (6.85 mL) and immersed in a cool water bath. The reaction mixture was stirred overnight (18 h) at ambient temperature to consume >95% of 5a according to gas chromatography (GC) analysis. Aqueous sodium bicarbonate (10 mL) was added to the reaction mixture and the layers were then thoroughly mixed and allowed to separate. The aqueous layer was extracted further with toluene (2×15 mL). The combined organic solution was dried over $Na_2SO_4$ and concentrated to afford 3.71 g of 6a. The crude product was flash-chromatographed and eluted with 1:9 ethyl acetate:heptane to afford 2.71 g (54% overall from 4a) of 6a.

$^1$H NMR (CDCl$_3$) δ 8.089 (d, 1H, J=8.24 Hz); 7.400 (d, 1H; J=1.10); 7.377 (dd, 1H, J=1.10, 8.24); 3.939 (s, 3H); 2.492 (s, 3H).

Example 10

Preparation of 1-(2-Thiomethyl-4-trifluoromethylphenyl)-3-cyclopropyl-1,3-propanedione (7) from Methyl 2-Thiomethyl-4-trifluoromethylbenzoate (6a)

Methyl 2-thiomethyl-4-trifluoromethylbenzoate (6a; 250 g; 10.0 mmol) and cyclopropyl methyl ketone (1.3 mL; 13.0 mmol; 1.3 equiv) were dissolved in 5 mL of dimethyl sulfoxide (DMSO). The mixture was cooled in an ice-water bath and a 60% dispersion of sodium hydride in mineral oil (0.48 g; 12.0 mmol; 1.2 equiv) was added all at once, resulting in gas evolution and an orange-brown color. The mixture was stirred in the ice bath for five minutes and then heated to 40° C. for 10 h, at which point gas chromatography (GC) analysis indicated no residual 6a. Toluene and 3 N HCl (10 mL) were added, and the mixture was thoroughly shaken and allowed to settle. The layers were separated and the aqueous solution was extracted with a further portion of toluene. The combined organic extracts were washed with saturated aqueous sodium bicarbonate (10 mL), dried with sodium sulfate, and concentrated. The crude product was filtered through a pad of flash silica gel (to remove the mineral oil) and eluted sequentially with 1:9 ethyl acetate:heptane and 1:4 ethyl acetate:heptane to afford 2.09 g (69%) of 7.

$^1$H NMR (CDCl$_3$) enol δ 7.632 (d, 1H, J=7.68 Hz); 7.468 (s, 1H); 7.411 (dd, 1H, J=1.65, 7.97 Hz); 6.100 (s, 1H); 2.507 (s, 3H); 1.755 (m, 1H); 1.23 (m, 2H); 1.0 (m, 2H); keto δ 7.916 (1H, d, J=8.24 Hz); 7.535 (s, 1H); 4.237 (s, 2H); 2.491 (s, 3H). FDMS (m/e): 302 (M$^+$).

Example 11

Preparation of 1-(2-Thiomethyl-4-trifluoromethylphenyl)-3-cyclopropyl-1,3-propanedione (7) from Butyl 2-Thiomethyl-4-trifluoromethylbenzoate (6b)

Butyl 2-thiomethyl-4-trifluoromethylbenzoate (6b; 2.08 g; 7.1 mmol) and cyclopropyl methyl ketone (0.92 mL; 9.2 mmol; 1.3 equiv) were dissolved in 3.5 mL of DMSO. The mixture was cooled in an ice-water bath and a 60% dispersion of sodium hydride in mineral oil (0.34 g; 8.5 mmol; 1.2 equiv) was added all at once, resulting in gas evolution and a reddish-orange color. The mixture was stirred in the ice bath for five minutes and then heated to 40° C. for 10 h, at which point thin layer chromatography (tlc) analysis indicated no residual 6b. Toluene (15 mL) and 3 N HCl (10 mL) were added, and the mixture was thoroughly shaken and allowed to settle. The layers were separated and the aqueous solution was extracted with a further portions of toluene (10 mL). The combined organic extracts were washed with saturated aqueous sodium bicarbonate (10 mL), dried with sodium sulfate and concentrated. The crude product was filtered through a pad of flash silica gel (to remove the mineral oil) and eluted sequentially with 1:9 ethyl acetate:heptane and 1:4 ethyl acetate:heptane to afford 1.75 g (82%) of 7.

$^1$ H NMR (CDCl$_3$) enol δ 7.632 (d, 1H, J=7.68 Hz); 7.468 (s, 1H); 7.411 (dd, 1H, J=1.65, 7.97 Hz); 6.100 (s, 1H); 2.507 (s, 3H); 1.755 (m, 1H); 1.23 (m, 2H); 1.0 (m, 2H); keto δ 7.916 (1H, d, J=8.24 Hz); 7.535 (s, 1H); 4.237 (s, 2H); 2.491 (s, 3H).

The claimed invention is:

1. A process for the preparation of a nitro-substituted aromatic carboxylic acid ester comprising the step of:

reacting a nitro-substituted aryl halide, in the absence of water and oxygen, with carbon monoxide and an alcohol in the presence of a metal catalyst and a proton acceptor to form the corresponding nitro-substituted aromatic carboxylic acid ester, wherein:
said aryl group of said nitro-substituted aryl halide is a substituted or unsubstituted, monocyclic or polycyclic aryl group or heteroaryl group containing at least one heteroatom of N, O, or S;
said carbon monoxide is present at a pressure of 14.7–1100 psi;
said alcohol is a linear or branched, substituted or unsubstituted $C_1$–$C_5$ alkyl alcohol;
said proton acceptor is a tertiary amine base; and
said metal catalyst is a homogeneous transition metal catalyst is prepared in situ by reacting a phosphine with a palladium compound in a ratio of about 1–6 atom equivalents of phosphorus per atom equivalent of palladium,
wherein:
said phosphine is selected from the group consisting of trimethylphosphine, triethylphosphine, tri-n-propylphosphine, tri-i-propylphosphine, tri-n-butylphosphine, tri-t-butylphosphine, tricyclohexylphosphine, triphenylphosphine, tri-o-tolylphosphine, methyldiphenylphosphine, 1,2-bis(diphenylphosphinoethane), and 1,3-bis(diphenylphosphino)propane; and
said palladium compound is selected from the group consisting of palladium(II) acetate, palladium(II) chloride, dichlorobis(acetonitrile)palladium(II), dichlorobis(benzonitrile)palladium(II), bis(dibenzylidineacetone)palladium(0), tris(dibenzylidineacetone)dipalladium(0), and tris(dibenzylidineacetone)dipalladium(0) chloroform adduct.

2. A process of claim 1, wherein said tertiary amine base is selected from the group consisting of triethylamine and tri-n-butylamine.

3. A process of claim 1, wherein said metal catalyst is dichlorobis(triphenylphosphine)palladium or dibromobis(triphenylphosphine)palladium present in an amount of between about 0.0005 to 0.5 molar equivalents based on said nitro-substituted aryl halide.

4. A process of claim 1, wherein said reacting step occurs in the presence of a solvent selected from the group consisting of an excess of said alcohol, an excess of said proton acceptor, an aliphatic hydrocarbon, an aromatic hydrocarbon, a cyclic ether, an acyclic ether, a polar aprotic solvent, and mixtures thereof.

5. A process of claim 1, wherein said nitro-substituted aryl halide is of formula (I):

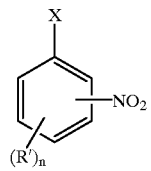

(I)

wherein
X is chloro, bromo, or iodo;
n is an integer of 1–4; and
R' is, independently, a $C_1$–$C_{10}$ alkyl group, a $C_2$–$C_{10}$ alkenyl group, a $C_2$–$C_{10}$ alkynyl group, a $C_4$–$C_{10}$ aryl or heteroaryl group, an ether, a thioether, a nitro, a trifluoromethyl, a fluoro, cyano, or acyl group; or together with the phenyl ring forms a substituted or unsubstituted fused polycyclic ring system; and
said corresponding nitro-substituted aromatic carboxylic acid ester is of formula (II):

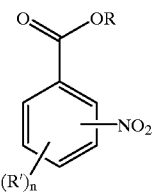

(II)

wherein
n and R' are as defined above; and
R is a $C_1$–$C_5$ alkyl group.

6. A process of claim 5, wherein n is 1, R' is a trifluoromethyl group, and R is a methyl or n-butyl group.

7. A process of claim 6, wherein R' is para to halide X of formula (I) and the nitro group is ortho to halide X of formula (I).

8. A process for the preparation of a thioether-substituted aromatic carboxylic acid ester comprising the steps of:
preparing a nitro-substituted aromatic carboxylic acid ester according to claim 1, and
reacting the said nitro-substituted aromatic carboxylic acid ester with a thiolate anion to form the corresponding thioether-substituted aromatic carboxylic acid ester.

9. A process of claim 8, wherein said thiolate anion is prepared in situ from a thiol and a base, wherein said base is selected from the group consisting of tertiary amines, alkali or alkaline earth metal hydroxides, and alkali or alkaline earth metal carbonates.

10. A process of claim 9, wherein said thiolate anion is a compound of the formula $R"S^-M^+$, wherein R" is a $C_1$–$C_{10}$ alkyl group or a $C_4$–$C_{10}$ aryl or heteroaryl group and M is selected from the group consisting of sodium, potassium and ammonium.

11. A process of claim 8, wherein said reacting step is conducted in a homogeneous solvent system comprising a water-immiscible solvent and water, or in a phase-transfer solvent system comprising a water-immiscible organic solvent, a phase-transfer catalyst, and, optionally, water.

12. A process of claim 11, wherein said reacting step is conducted in a phase-transfer solvent system wherein said phase-transfer catalyst is a tetralkylammonium or tetralkylphosphonium salt selected from the group consisting of tetrabutylammonium bromide, tetrabutylammonium chloride, methyltributylammonium chloride, methyl trioctylammonium chloride, and tetrabutylphosphonium bromide; and said water-immiscible solvent is selected from the group consisting of an aliphatic hydrocarbon, an aromatic hydrocarbon, a cyclic ether, and an acyclic ether.

13. A process of claim 10, wherein said nitro-substituted aromatic carboxylic acid ester is of formula (II):

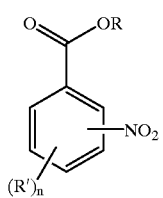

(II)

wherein
n is an integer of 1–4;
R' is, independently, a $C_1$–$C_{10}$ alkyl group, a $C_2$–$C_{10}$ alkenyl group, a $C_2$–$C_{10}$ alkynyl group, a $C_4$–$C_{10}$ aryl or heteroaryl group, an ether, a thioether, a nitro, a trifluoromethyl, a fluoro, cyano, or acyl group; or together with the phenyl ring forms a substituted or unsubstituted fused polycyclic ring system; and
R is a $C_1$–$C_5$ alkyl group; and
said corresponding thioether-substituted aromatic carboxylic acid ester is of formula (III):

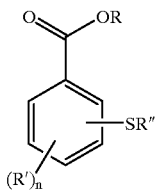

(III)

wherein
n, R', and R are as defined above.

14. A process of claim 13, wherein R' is para to the ester group of formula (II) and the nitro group is ortho to the ester group of formula (II).

15. A one-pot process for the preparation of a thioether-substituted aromatic carboxylic acid ester comprising the steps of:
reacting a nitro-substituted aryl halide, in the absence of water and oxygen, with carbon monoxide and an alcohol in the presence of a metal catalyst and a proton acceptor to form the corresponding nitro-substituted aromatic carboxylic acid ester,
wherein:
said aryl group of said nitro-substituted aryl halide is a substituted or unsubstituted, monocyclic or polycyclic aryl group or heteroaryl group containing at least one heteroatom of N, O, or S;
said carbon monoxide is present at a pressure of 14.7–1100 psi;
said alcohol is a linear or branched, substituted or unsubstituted $C_1$–$C_5$ alkyl alcohol;
said proton acceptor is a tertiary amine base; and
said metal catalyst is a homogeneous transition metal catalyst is prepared in situ by reacting a phosphine with a palladium compound in a ratio of about 1–6 atom equivalents of phosphorus per atom equivalent of palladium,
wherein:
said phosphine is selected from the group consisting of trimethylphosphine, triethylphosphine, tri-n-propylphosphine, tri-i-propylphosphine, tri-n-butylphosphine, tri-t-butylphosphine, tricyclohexylphosphine, triphenylphosphine, tri-o-tolylphosphine, methyldiphenylphosphine, 1,2-bis(diphenylphosphinoethane), and 1,3-bis(diphenylphosphino)propane; and
said palladium compound is selected from the group consisting of palladium(II) acetate, palladium(II) chloride, dichlorobis(acetonitrile)palladium(II), dichlorobisfbenzonitrile)palladium(II), bis(dibenzylidineacetone)palladium(0), tris(dibenzylidineacetone)dipalladium(0), and tris(dibenzylidineacetone)dipalladium(0) chloroform adduct; and
reacting without isolating said corresponding nitro-substituted aromatic carboxylic acid ester with a thiolate anion to form the corresponding thioether-substituted aromatic carboxylic acid ester.

16. A compound of butyl 2-nitro-4-trifluoromethylbenzoate.

* * * * *

UNITED STATES PATENT AND TRADEMARK OFFICE
CERTIFICATE OF CORRECTION

PATENT NO.   : 6,337,418 B1
DATED        : January 8, 2002
INVENTOR(S)  : Neil W. Boaz et al.

It is certified that error appears in the above-identified patent and that said Letters Patent is hereby corrected as shown below:

Column 16,
Line 50, the term "water immiscible" should read -- water-miscible --

Column 18,
Line 32, the term "dichlorobisfbenzonitrile)palladium(II)," should read
-- dichlorobis(benzonitrile)palladium(II) --

Signed and Sealed this

Third Day of September, 2002

Attest:

Attesting Officer

JAMES E. ROGAN
Director of the United States Patent and Trademark Office